United States Patent [19]

Nash et al.

[11] Patent Number: 5,306,254

[45] Date of Patent: Apr. 26, 1994

[54] VESSEL POSITION LOCATING DEVICE AND METHOD OF USE

[75] Inventors: John Nash, Downingtown; Douglas Evans, Devon, both of Pa.; John J. Fleischhacker, Minnetonka, Minn.

[73] Assignee: Kensey Nash Corporation, Exton, Pa.

[21] Appl. No.: 955,095

[22] Filed: Oct. 1, 1992

[51] Int. Cl.⁵ .............................................. A61M 5/00
[52] U.S. Cl. .................................. 604/168; 128/772
[58] Field of Search ............... 128/763, 765, 770, 771; 604/164, 165, 168, 170

[56] References Cited

U.S. PATENT DOCUMENTS

| | | |
|---|---|---|
| 4,525,157 | 6/1985 | Vaillancourt ...................... 604/168 |
| 4,655,750 | 4/1987 | Vaillancourt ...................... 604/168 |
| 4,772,264 | 9/1988 | Cragg ................................. 604/168 |
| 4,863,431 | 9/1989 | Vaillancourt ...................... 604/168 |
| 4,904,240 | 2/1990 | Hoover .............................. 604/168 |
| 4,961,729 | 10/1990 | Vaillancourt ...................... 604/168 |

*Primary Examiner*—Max Hindenburg
*Attorney, Agent, or Firm*—Caesar, Rivise, Bernstein, Cohen & Pokotilow, Ltd.

[57] ABSTRACT

A device for determining the location of the wall of an artery in a living being via a percutaeous incision or puncture. The device comprises an elongated tubular member having a distal end portion, a proximal end portion, and a passageway extending therethrough for receipt of a guide wire. The device is inserted through an introducer sheath having an open distal end into said percutaneous incision or puncture over said guide wire so its distal end portion is located within the artery and its proximal end portion is located outside of the body of the being. The has two liquid entrance ports in its distal end portion and one liquid outlet port in its proximal end portion. The liquid entrance ports and outlet port are in communication with each other through the device's passageway. When the device is positioned within the introducer sheath and the entrance ports are located beyond the open distal end of the introducer sheath and within the artery blood flows into the entrance ports through passageway and out through the outlet port so that it can be observed. The device and introducer sheath are then retracted until the flow of blood out of the outlet port stops, thereby indicating the location of the artery wall.

14 Claims, 3 Drawing Sheets

VESSEL POSITION LOCATING DEVICE AND METHOD OF USE

BACKGROUND OF THE INVENTION

In a United States patent application Ser. No. 07/846,322, filed on Mar. 5, 1992, entitled Hemostatic Puncture Closure System and Method of use, which has been assigned to the same assignee as this invention, and whose disclosure is incorporated by reference herein, there is disclosed a system including a closure device and method of use for sealing a small incision or puncture in tissue separating one portion of the body of a living being from another portion thereof, e.g., a percutaneous puncture in a artery, to prevent the flow of a body fluid, e.g., blood, through the puncture. The closure device comprises three components, namely, an anchor member, a sealing member, and a filament, e.g., suture. The sealing member is formed of a hemostatic material, e.g., compressed collagen foam. The anchor member includes a tissue engaging portion configured to pass through the puncture in one direction but resistant to passage therethrough in the opposite direction. The sealing member includes a tissue engaging portion. The filament is connected between the anchor member and the sealing member in a pulley-like arrangement so that they may be moved relative to each other by the application of a pulling force on the filament.

The means for introducing the closure into the percutaneous incision or puncture comprises a tubular member having a distal free end arranged to be inserted into the puncture tract and through the puncture in the vessel. A closure carrier is arranged to be inserted through the tubular introducer member to expel the anchor member of the closure therefrom and to draw it into engagement with the distal free end of the tubular introducer member. The introducer member and the closure carrier are arranged to be moved together to draw the closure anchor into engagement with the interior tissue of the blood vessel contiguous with the puncture. The filament is arranged to be pulled to pull the closure's anchor and its sealing member relative to each other to cause the sealing member to engage tissue contiguous with the puncture outside of the vessel.

The system disclosed and claimed in that application includes various types of position detecting devices and a method of use to enable one to readily determine the location of the wall of the vessel or lumen by the percutaneous introduction of the device into the vessel or lumen. Those devices are disclosed as suitable for use as part of a system or method to seal a percutaneous puncture or incision in a vessel or lumen or may be used for other purposes, e.g., they may be used for any application wherein it is desirable to determine the location of a vessel or lumen wall via a percutaneous incision or puncture.

While the position indicating devices disclosed and claimed in the foregoing patent application are suitable for their intended purposes, they never the less leave something to be desired from the standpoint of simplicity of construction and ease of use.

OBJECTS OF THE INVENTION

Accordingly, it is a general object of this invention to provide a device and methods of use which overcome the disadvantages of the prior art.

It is a further object of this invention to provide devices and methods of use for enabling one to determine the location of the wall of a blood vessel or other lumen through a percutaneous incision or puncture.

It is still another object of this invention to provide a devices which is simple in construction and easy to use to enable one to determine the location of the wall of a blood vessel or other lumen through a percutaneous incision or puncture.

SUMMARY OF THE INVENTION

These and other objects of this invention are achieved by providing a device and method of use for determining the location of the wall of a vessel or lumen in a living being via a percutaneous incision or puncture.

The device comprises an elongated tubular member having a distal end portion, a proximal end portion and a passageway extending therethrough for receipt of a guide wire. The device is arranged to be inserted through an introducer sheath having an open distal end into the percutaneous incision or puncture over the guide wire so that the proximal end portion of the device is located within the vessel or lumen and the distal end portion is located outside of the body of the being.

The device has at least one liquid entrance port located adjacent to the distal end portion and a liquid outlet port located adjacent the proximal end portion. The liquid entrance port(s) is(are) in fluid communication with the passageway, while the outlet port is also in fluid communication with the passageway.

When the device is positioned within the introducer sheath and the entrance port is located beyond the open distal end of the introducer sheath and within the vessel or lumen liquid within the vessel or lumen may flow into the entrance port through the passageway and out through the outlet port.

In accordance with the method of this invention once the device and the introducer sheath are in the position at which the liquid flows out of the outlet port the device and the introducer sheath are then moved together outward with respect to the vessel or lumen until the entrance port is located outside the vessel or lumen at which time the flow of liquid through the outlet port ceases, thereby indicating the location of the vessel or lumen wall.

If the device is to be used for inserting a closure in the incision or puncture to seal it the device and introducer sheath are then moved together inward a slight distance, e.g., 1 cm., to ensure that the open distal end of introducer sheath is again located within the vessel or lumen, at which time the device may be removed.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein.

DETAILED DESCRIPTION OF THE PREFERRED EMBODIMENT

Figure 1:
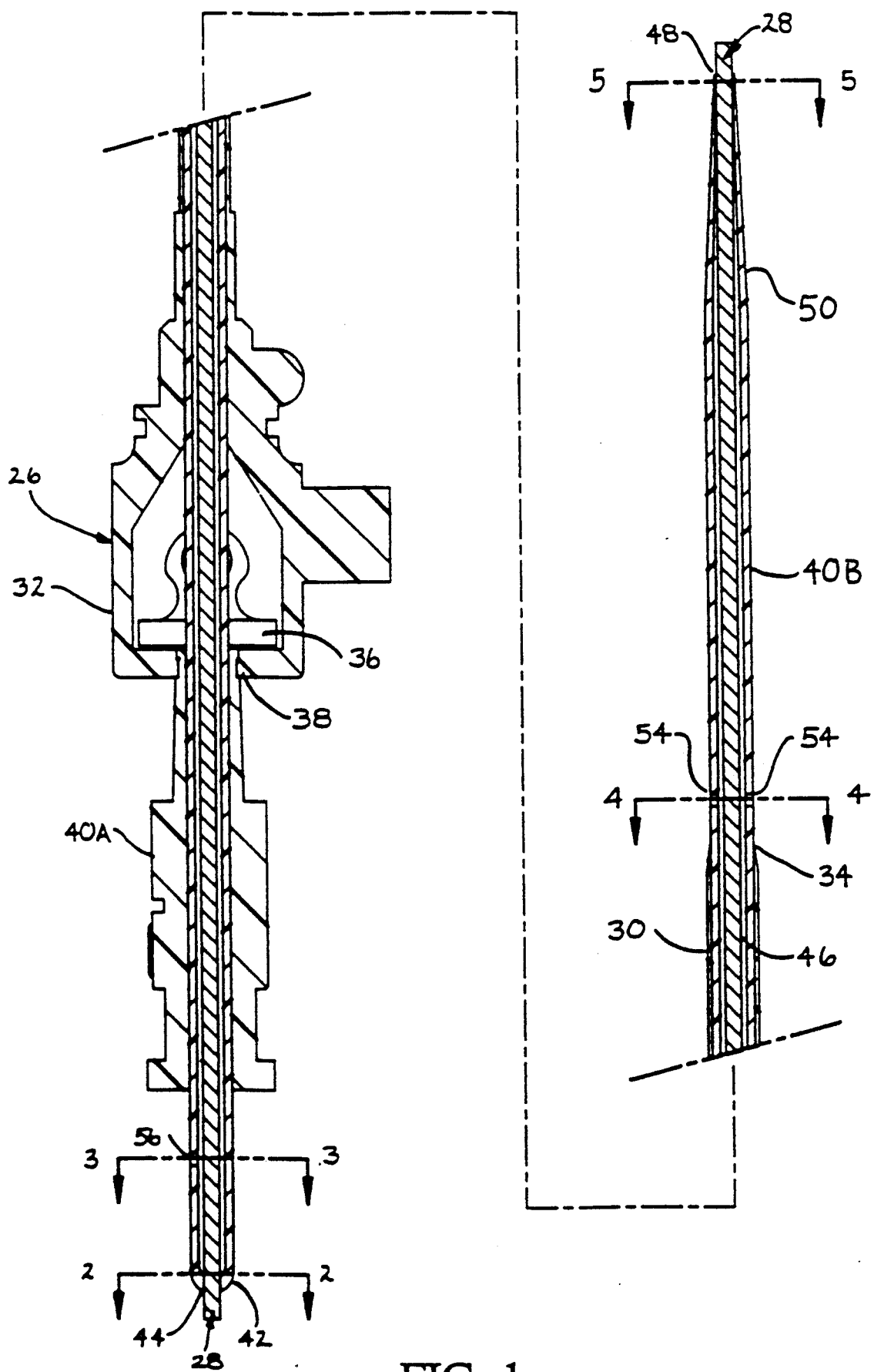
FIG. 1 is a longitudinal sectional view of a blood vessel wall locator constructed in accordance with the teachings of this invention shown extending through a conventional introducer sheath and with a guide wire extending through the locator.
Figures 2, 3, 4, 5:
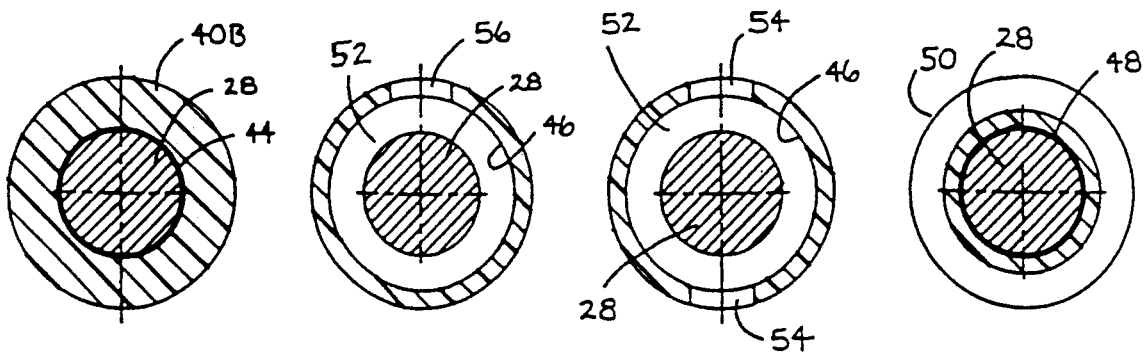
FIG. 2 is a enlarged sectional view taken along line 2—2 of FIG. 1.
FIG. 3 is a enlarged sectional view taken along line 3—3 of FIG. 1.
FIG. 4 is a enlarged sectional view taken along line 4—4 of FIG. 1.
FIG. 5 is a enlarged sectional view taken along line 5—5 of FIG. 1.

Referring now in greater detail to the various figures of the drawings wherein like reference characters refer to like parts, there is shown at 20 a device for detecting the location of the wall 22 (FIGS. 6-8) of a blood vessel, in a living being via a percutaneous incision or puncture 24 extending into the vessel or lumen. The puncture 24 includes not only the opening in the wall of the vessel but also the tract 24A, i.e., the passageway in the tissue located between the vessel and the skin of the being formed when the vessel is punctured.

The device 20 has particular utility when used in connection with closure devices for sealing percutaneous incisions or punctures in arteries, such as those disclosed and claimed in the aforementioned patent application, after intravascular procedures, such as angiographic dye injection, cardiac catheterizations, balloon angioplasty and other types of recanalizing of atherosclerotic arteries, etc., have been accomplished. However, it should be understood by those skilled in the art that the device 20 can be used anytime it is necessary to detect the location of a blood vessel in the patient's body. In fact, the subject invention can be configured for use to detect the location of any lumen or duct carrying a liquid in the patient's body.

When used in blood vessel puncture sealing applications a conventional introducer sheath 26, like that shown in FIGS. 1 and 6-8, is located within the percutaneous incision or puncture 24 and 24A to a desired position with respect to the artery wall 22 so that the closure (not shown) can be introduced through that introducer into the puncture or incision to seal the puncture or incision. The device 20 of this invention facilitates the location of the sheath 26 at the desired position. To achieve that end the device 20 is arranged to be used with a conventional guide wire 28 and the introducer sheath 26 so that the distal end of the introducer sheath can be located just within the artery's wall.

Before describing the locator 20 of this invention a brief description of the introducer sheath 26 and the guide wire 28 is in order. Thus, as can be seen in FIG. 1 the introducer sheath is of any conventional construction, formed of any suitable material, e.g., plastic, and includes a flexible tubular extension 30 mounted on a hollow housing body 32. The distal end of the sheath extension is open at 34. A hemostasis valve 36 is located within the body 32 and in communication with a centrally located access port 38. The guide wire 28 is also of any conventional construction and comprises an elongated, flexible member of constant circular cross-sectional area.

As can be seen in FIG. 1 the blood vessel locator device 20 basically comprises an elongated tubular member 40B and a body 40A. The body 40A is formed of any suitable rigid material, e.g., high density polyethylene, and includes a central passageway extending therethrough. The tubular member 40B is formed of any suitable, relatively flexible material, e.g., polyethylene, polytetrafluroethylene (TEFLON), polyurethane, and extends through the passageway in the device's body 40B and is fixedly secured thereto. The tubular member 40B has a rounded proximal end 42 including a circular, centrally located guide wire entrance hole 44. The distal end portion of the tubular member 40 tapers downward and terminates at its free end in a centrally located guide wire exit hole 48. A central passageway 46 extends down the length of the tubular member 40B from the hole 44 to the hole 48. The distal end portion of the passageway 46 also tapers downward toward the exit hole 48. In fact, the inside diameter of the exit hole 48 is the same as that of the entrance hole 44, while the remaining portion of the passageway is of substantially greater inside diameter that the outside diameter of the guide wire. Accordingly, when the guide wire 28 is extended through the passageway 46 in the device 20 an annular space 52 for carrying blood therethrough (as will be described later) is created between the inner surface of the device 20 and the outer surface of the guide wire.

In accordance with a preferred embodiment of this invention the inside diameter of the inlet and outlet holes 44 and 48, respectively, are only marginally larger than the outside diameter of the guide wire 28 to ensure that blood does not flow through the interface between them and the guide wire when the device 20 is in place in the artery, as will be described later. To that end, in one preferred embodiment of this invention, the outside diameter of the guide wire is 0.038 inch (0.96 mm), while the inside diameter of the entrance and exit holes 44 and 48, respectively, is 0.040 inch (1.02 mm). Moreover, the inside diameter of the central passageway 46 is 0.060 inch (1.52 mm).

A pair of blood inlet ports 54 are provided at diametrically opposed positions in the wall of the tubular member 40B. The inlet ports 54 communicate with the annular space 52. The inlet ports are arranged to lie just distally, e.g., 0.50 inch (0.127 cm), from the open end 34 of the introducer sheath 30 when the device 20 is in position therein. At this time the body 40A of the device 20 will abut the proximal end of the introducer sheath's housing 32.

A blood outlet port 56 is provided through the wall of the member 40 a short distance, e.g., 0.50 inch (1.27 cm), from the proximal end of the tubular member 40B and also communicates with the annular space 52. The outlet port 56 is located proximally of the device's body portion 40A when the device is in position in the introducer sheath 26.

Figure 6:
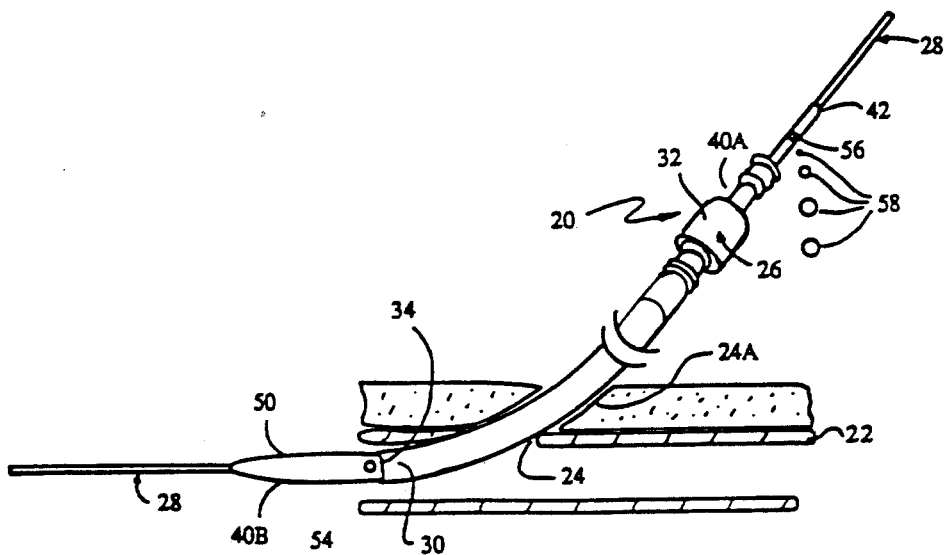
FIGS. 6, 7, and 8 are illustrations showing the sequential steps in the use of the blood vessel locator of the subject invention.

In order to correctly position the introducer sheath 26 within the interior of the artery so that a closure (not shown) can be inserted in the artery to seal the incision or puncture, the location of the artery wall 22 must be established. This is accomplished by threading the device 20 on the guide wire 28 and sliding the device 20 along the guide wire 28 through the introducer's sheath 30, and its interiorly located hemostasis valve 36, until the entrance ports 54 of the device 20 extend beyond the open free end 34 of the introducer sheath and within the hollow interior of the artery 24 as shown in FIG. 6.

Since the entrance ports 54 are in fluid communication with the passageway 46 in the device 20, blood will flow into those ports and through the annular space 52 to the outlet port 56, whereupon blood droplets 58 will drip therefrom. In this regard the blood will normally flow out of the outlet port 56 by virtue of the pressure differential across the artery wall. If however, there is insufficient pressure to cause such a flow of blood some means (not shown) can be used to create the desired differential pressure, e.g., suction can be used.

Figure 7:
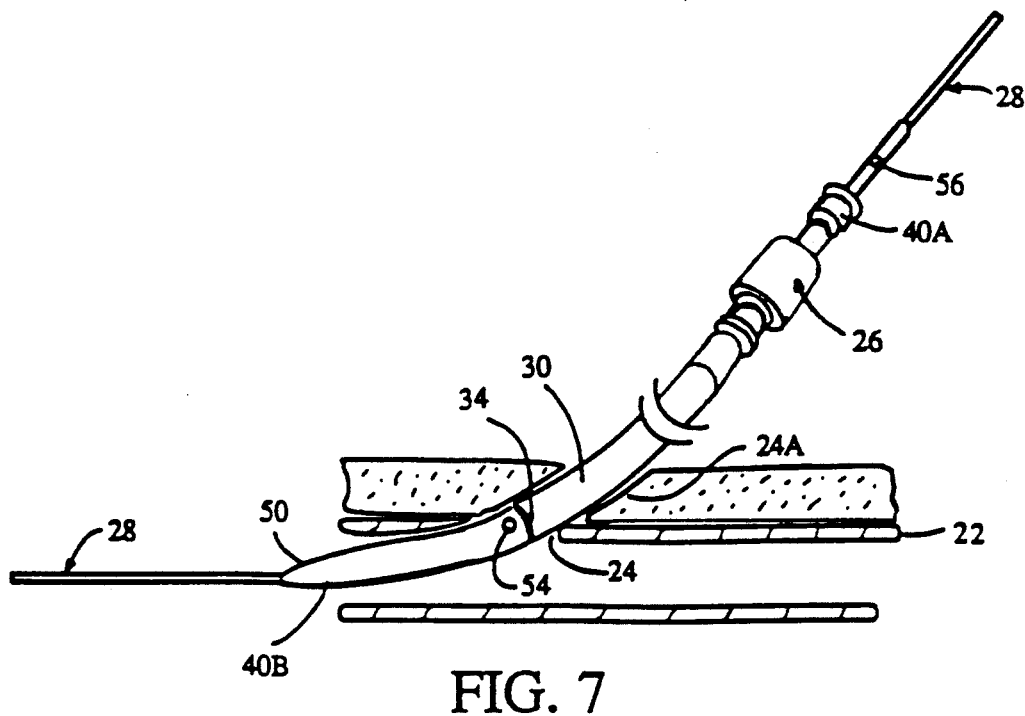

In any event once the flow of blood is observed exiting the outlet port 56 the introducer sheath 26 (with the device 20 therein) is then retracted, i.e., moved proximally, until the blood flow through the outlet port 56 just stops as shown in FIG. 7. This indicates that the distal end 32 of the introducer sheath has just left the interior of the artery lumen.

Figure 8:
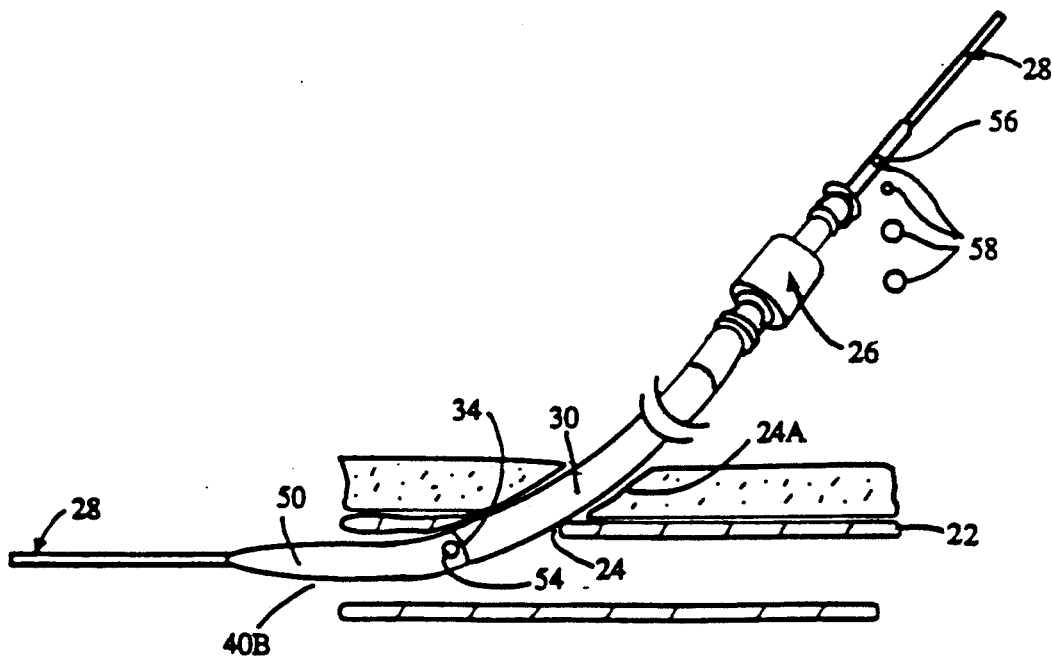

The introducer sheath 26 with the device 20 therein is then reinserted, i.e., moved distally, approximately 1 cm into the puncture, as shown in FIG. 8, to ensure that the open distal end 34 of introducer sheath is back within the interior of the artery lumen, i.e., at the desired position within the artery for introduction of the closure. Blood flow should be reestablished through the outlet port 56 this time, i.e., the droplets 58 will again form.

As should be appreciated by those skilled in the art that once the flow of blood restarts the position of the artery wall will be known, and the introducer sheath precisely positioned therein for effecting the sealing of the artery puncture utilizing the teachings of the aforementioned patent application. To achieve that end the device 20 is then removed from the introducer sheath to ready the introducer sheath for receipt of the deployment instrument (not shown) carrying the closure device (not shown).

Without further elaboration the foregoing will so fully illustrate our invention that others may, by applying current or future knowledge, adopt the same for use under various conditions of service.

What is claimed is:

1. A device for use with a guide wire and an introducer sheath having an open distal end for determining the location of the wall of a vessel or lumen in a living being via a percutaneous incision or puncture through which said guide wire and sheath extend, said device comprising an elongated tubular member having a cylindrical side wall including an inner surface defining a passageway extending longitudinally through said member, a distal end portion including an opening therein, and a proximal end portion including an opening therein, said passageway being configured for receipt of said guide wire, whereupon said guide wire extends through said openings and a fluid space is created between said inner surface of said side wall and said guide wire, said tubular member having at least one liquid entrance port extending through said side wall adjacent said distal end portion and a liquid outlet port extending through said side wall adjacent said proximal end portion, said at least one liquid entrance port being in fluid communication with said fluid space when said guide wire is received within said passageway, said outlet port being in fluid communication with said fluid space when said guide wire is received within said passageway, whereupon when said device is positioned within said introducer sheath and said at least one entrance port is located beyond said open distal end of said introducer sheath and within said vessel or lumen, liquid within said vessel or lumen may flow into said entrance port through a portion of said fluid space and out through said outlet port.

2. The device of claim 1 wherein said device includes a free distal end, with said passageway extending therethrough, said passageway at said free distal end being substantially the same diameter as that of said guide wire so that liquid within said vessel or lumen may not gain ingress into said passageway from said distal end when said guide wire is extended therethrough.

3. The device of claim 2 wherein said distal end portion of said tubular member includes a distal free end which is tapered, and wherein said opening is located at said distal free end.

4. The device of claim 2 wherein said outlet port is visible to the user of said apparatus so that liquid flowing out of said outlet port may be observed.

5. The device of claim 4 wherein said distal end portion of said tubular member includes a distal free end which is tapered, and wherein said opening is located at said distal free end.

6. The device of claim 2 wherein said device is relatively flexible to permit it to bend when inserted within said vessel or lumen.

7. The device of claim 1 wherein said outlet port is visible to the user of said apparatus so that liquid flowing out of said outlet port may be observed.

8. The device of claim 7 wherein said distal end portion of said tubular member includes a distal free end which is tapered, and wherein said opening is located at said distal free end.

9. The device of claim 1 wherein said distal end portion of said tubular member includes a distal free end which is tapered, and wherein said opening is located at said distal free end.

10. The device of claim 1 wherein said device is relatively flexible to permit it to bend when inserted within said vessel or lumen.

11. A method of determining the location of the wall of a vessel or lumen of a living being by use of a position detecting device, a guide wire, and an introducer sheath, said position detecting device comprising an elongated tubular member having a passageway extending therethrough, a distal end portion having at least one entrance port in fluid communication with said passageway, and a proximal end portion in fluid communication with said passageway, said introducer sheath having an open distal end, said method comprising placing said sheath within said incision or puncture so that said open distal end is located within said vessel or lumen, disposing said position detecting device within said introducer sheath with said guidewire extending through said passageway so that said at least one entrance port extends beyond the open end of said introducer sheath and is within said vessel or lumen and in communication with any liquid therein to enable said liquid to flow into said at least one entrance port, through said passageway and out of said outlet port, thereafter moving said introducer sheath and said position detecting device together outward from said vessel or lumen, and sensing when said flow of liquid therethrough said outlet port ceases, thereby indicating that said at least one entrance port is no longer located within said interior of said vessel or lumen.

12. The method of claim 11 additionally comprising the step of moving said introducer sheath and said position detecting device together inward into said vessel or lumen a small distance, and sensing when said flow of liquid therethrough said outlet port restarts, thereby indicating that said at least one entrance port is again located within said interior of said vessel or lumen.

13. The method of claim 12 wherein said method comprises determining the location of the wall of a blood vessel.

14. The method of claim 11 wherein said method comprises determining the location of the wall of a blood vessel.

* * * * *